United States Patent
Hendrick

(10) Patent No.: US 10,525,235 B2
(45) Date of Patent: Jan. 7, 2020

(54) WIRE CENTERING SHEATH AND METHOD

(71) Applicant: The Spectranetics Corporation, Colorado Springs, CO (US)

(72) Inventor: Brandon Thomas Hendrick, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 150 days.

(21) Appl. No.: 15/646,501

(22) Filed: Jul. 11, 2017

(65) Prior Publication Data
US 2017/0304592 A1    Oct. 26, 2017

Related U.S. Application Data

(62) Division of application No. 13/798,985, filed on Mar. 13, 2013, now Pat. No. 9,731,098.

(51) Int. Cl.
| A61M 25/04 | (2006.01) |
| A61B 17/3207 | (2006.01) |
| A61M 25/01 | (2006.01) |
| A61M 25/00 | (2006.01) |
| A61B 34/00 | (2016.01) |
| A61B 17/22 | (2006.01) |

(52) U.S. Cl.
CPC ......... *A61M 25/04* (2013.01); *A61B 17/3207* (2013.01); *A61B 34/70* (2016.02); *A61B 2017/22068* (2013.01); *A61M 25/0102* (2013.01); *A61M 2025/0096* (2013.01)

(58) Field of Classification Search
CPC ..................... A61M 25/0074; A61M 25/0082
See application file for complete search history.

(56) References Cited

U.S. PATENT DOCUMENTS

| 7,329,267 B2 | 2/2008 | Weber |
| 9,731,098 B2 | 8/2017 | Hendrick |
| 2007/0232981 A1 | 10/2007 | Ravenscroft et al. |
| 2009/0137867 A1 | 5/2009 | Goto |
| 2013/0116715 A1 | 5/2013 | Weber |

*Primary Examiner* — Katherine M Shi
*Assistant Examiner* — Michael G Mendoza

(57) ABSTRACT

The present disclosure is directed, in one embodiment, to a wire centering sheath system in which wires outwardly extend from a sheath to brace against a vessel wall. The wire centering sheath system may be used to center endovascular devices.

11 Claims, 5 Drawing Sheets

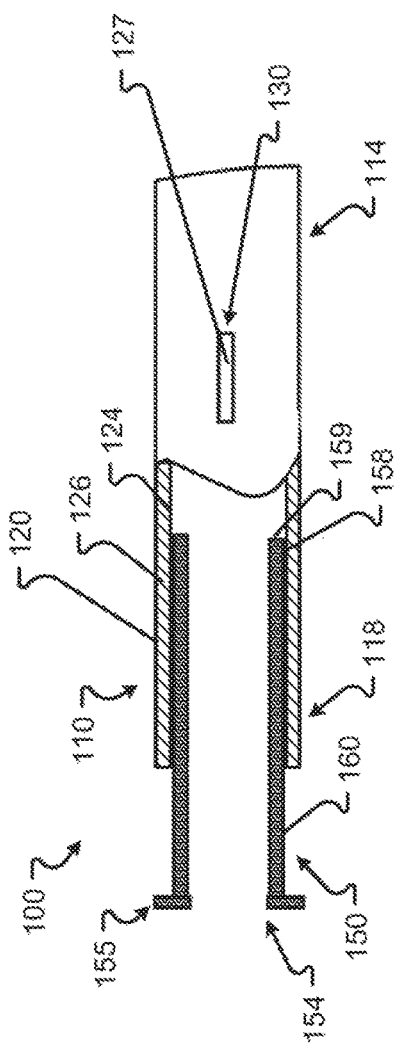
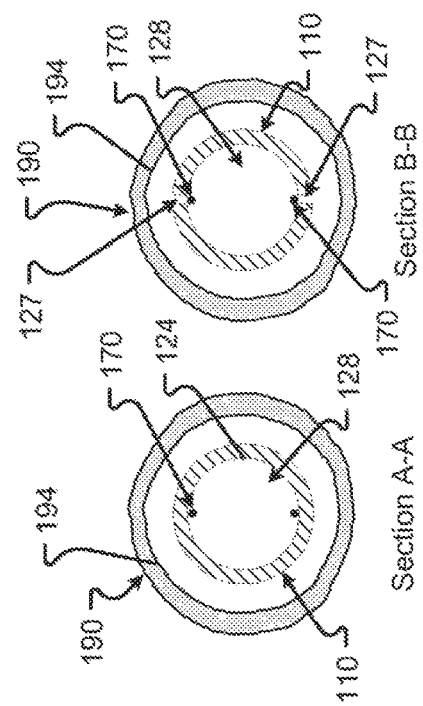
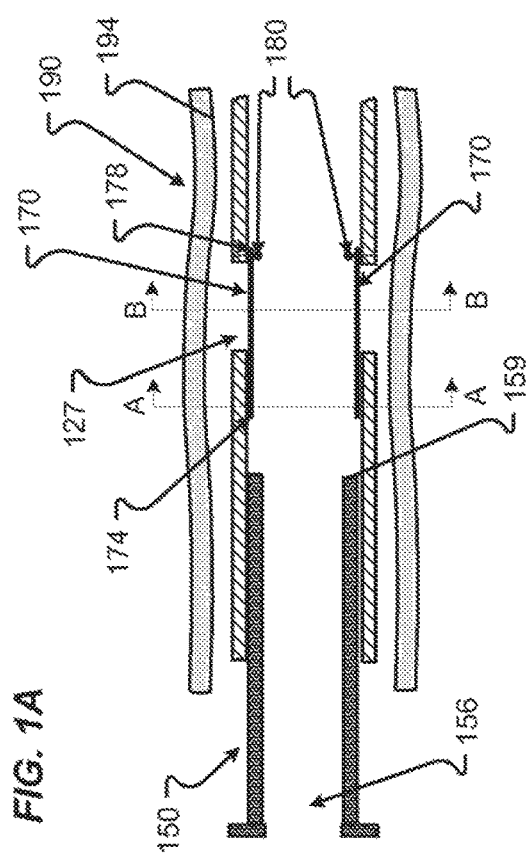

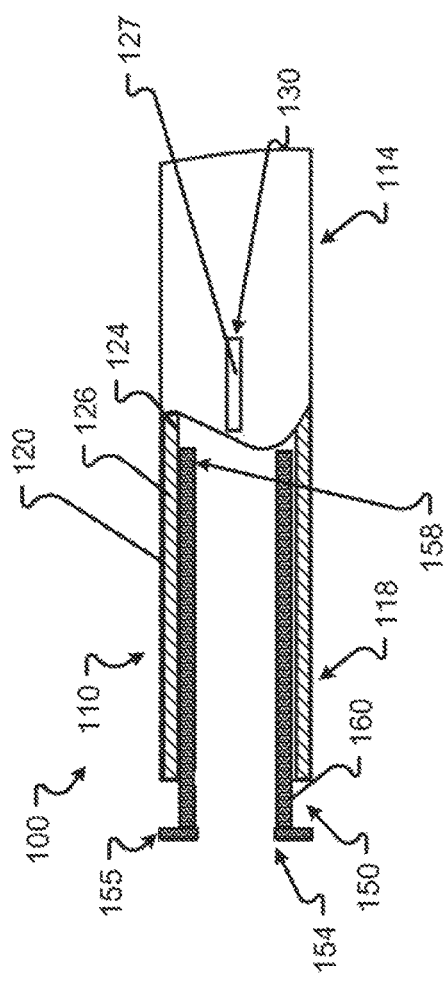
FIG. 2A
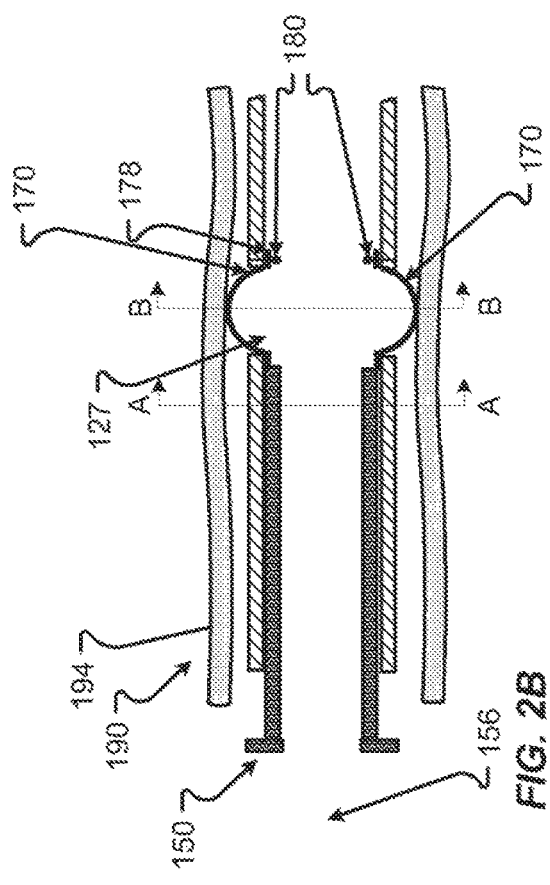
FIG. 2B
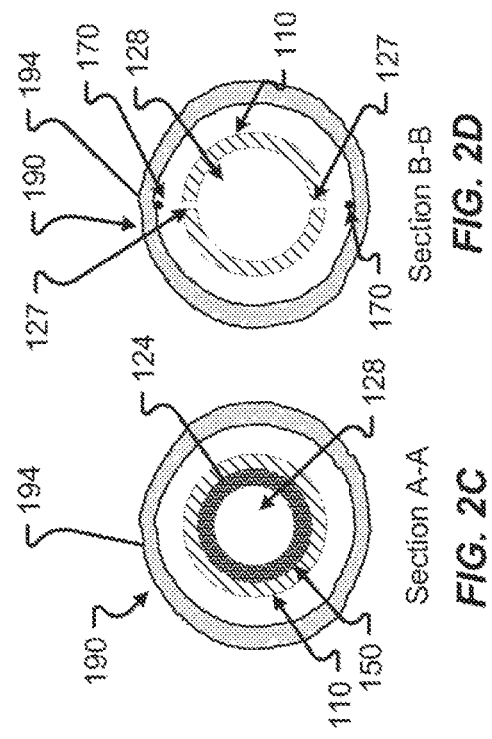
Section A-A
FIG. 2C
Section B-B
FIG. 2D

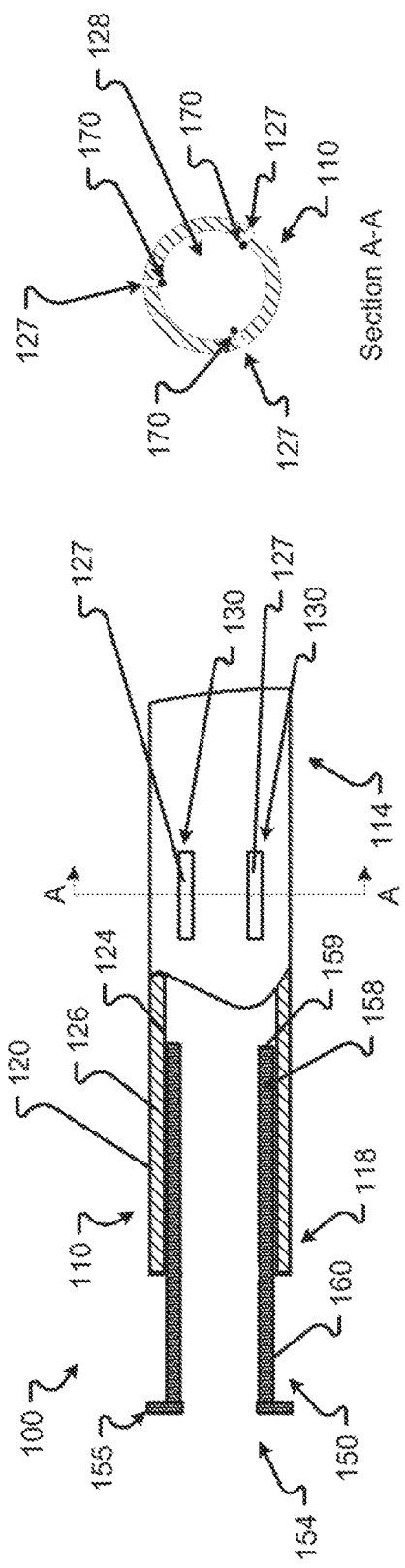
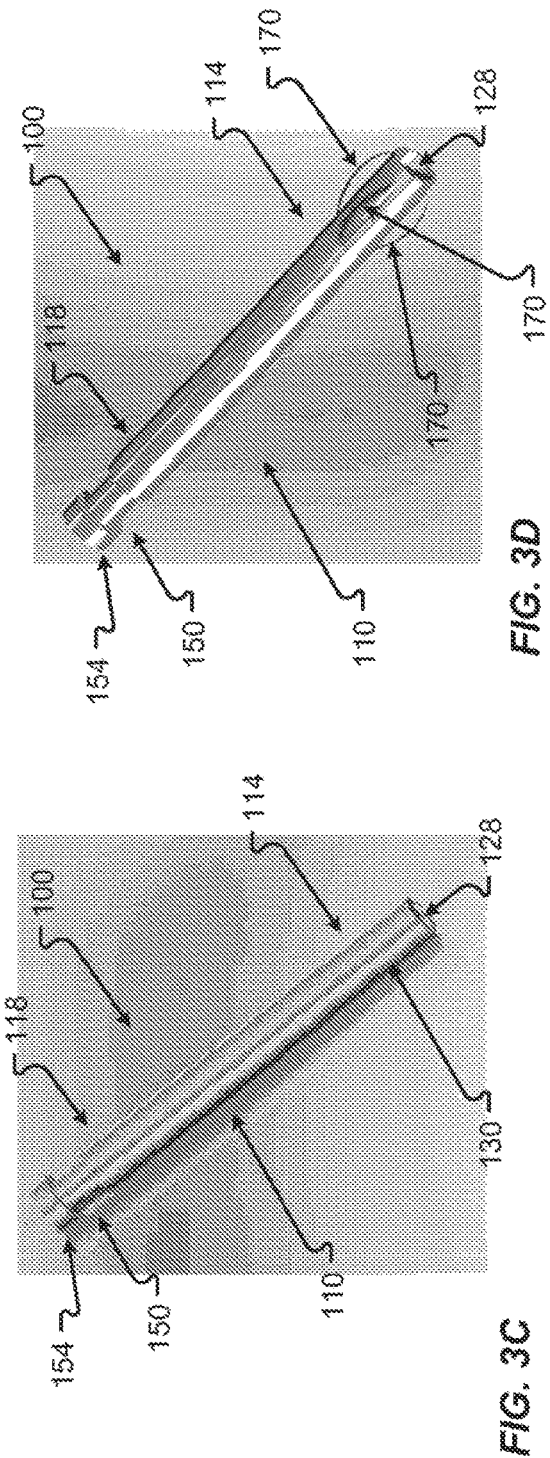
FIG. 3A
FIG. 3B
FIG. 3C
FIG. 3D

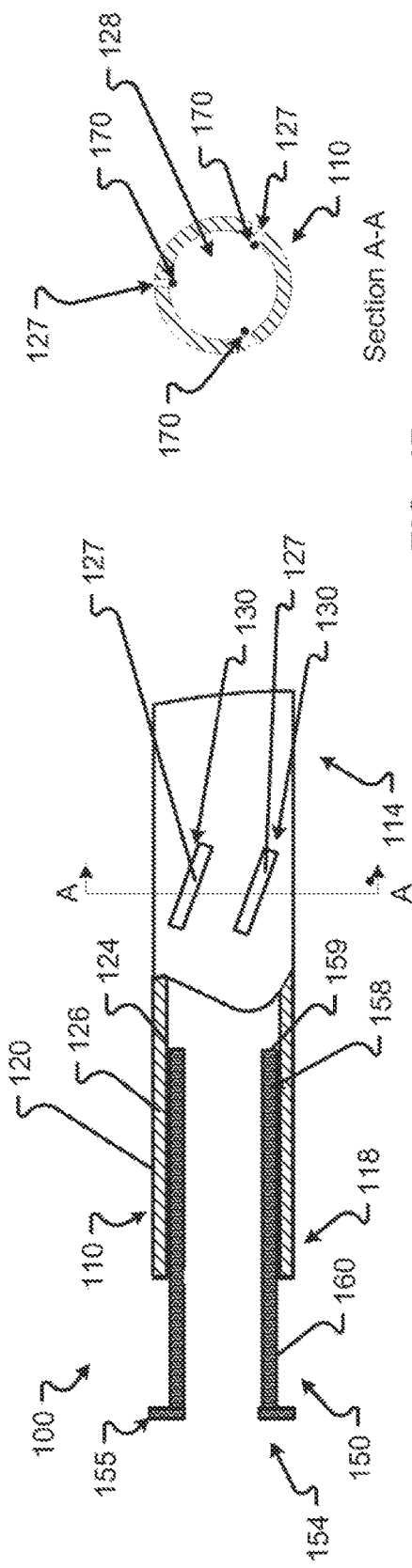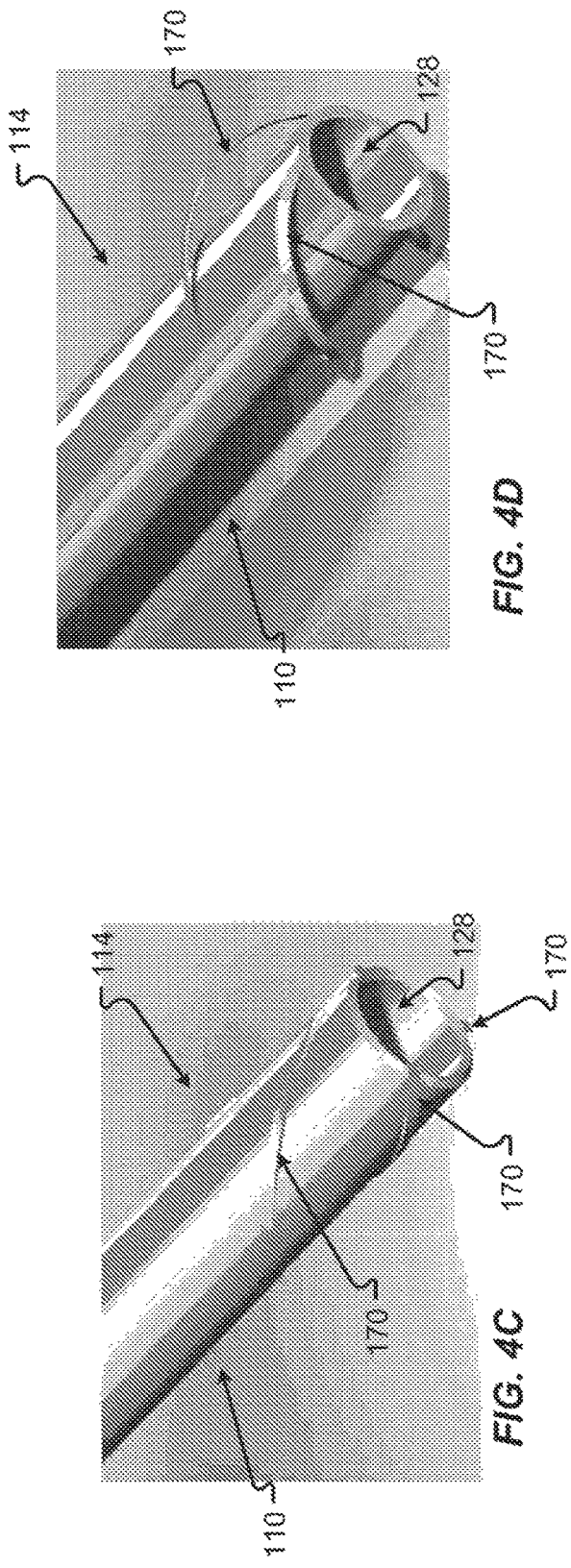
FIG. 4A
FIG. 4B
FIG. 4C
FIG. 4D

WIRE CENTERING SHEATH AND METHOD

CROSS REFERENCE TO RELATED APPLICATION

The present application is a divisional of U.S. application Ser. No. 13/798,985, entitled "WIRE CENTERING SHEATH AND METHOD", filed on Mar. 13, 2013, now U.S. Pat. No. 9,731,098, which is hereby incorporated herein by reference in its entirety for all that it teaches and for all purposes.

FIELD

The disclosure relates generally to surgical devices and particularly to centering of endovascular devices.

BACKGROUND

There is a frequent need to center medical instruments or delivery devices such as catheters or wires during surgical procedures. For example, during endovascular interventions it is desired to reliably, accurately and robustly position an intervention device within the body channel, such as when attempting to clear atherosclerotic plaque which can build up on artery walls. It is also desirable to first engage the middle of a lesion within a vascular channel with an instrument before controllably retracting in order to reduce the risk of sub-intimal entry or perforation.

Catheters are used ubiquitously in medical procedures. For example, catheters are used to diagnose many abnormalities, to treat vascular disease, to perform vascular interventions, to deliver devices to occlude vessels and to focally deliver agents to tissues. The catheter technology employed will vary depending on the surgical procedure and the nature and extent of the injury. Many times the stability of the catheter tip is not problematic or critical to the procedure, but routinely the stability of the catheter tip is indeed important to the success of the particular procedure. In many cases a "guide" catheter is inserted and the tip is placed within or near the orifice of the vessel intended to be treated.

The typical approach to center a medical instrument or delivery device, such as catheters, within a body channel or secure its robust positioning involves guiding by balloons or deflection of the instrument sheath itself. Such an approach is difficult to safely and accurately control, and generally does not effectively center the medical instrument.

Therefore, it is desired to have a device and method of reliably, accurately and effectively centering a medical instrument or delivery device such as a catheter or wire during surgical procedures.

SUMMARY

These and other needs are addressed by the various embodiments and configurations of the present disclosure. The present disclosure is directed to a wire centering sheath system in which wires outwardly extend from a sheath to brace against a vessel wall. The wire centering sheath system may be used to center endovascular devices.

In one embodiment, a wire centering sheath device is disclosed, the device comprising: (a) a shaft, the shaft having a proximal end, a distal end, a sidewall at least two slots forming at least two voids in the sidewall, and at least two centering wires connected to the shaft and disposed adjacent to the at least two slots, wherein the shaft includes a shaft inner lumen running from the proximal end to the distal end; (b) a hollow rod adapted for inserting into the proximal end of the shaft, the rod having a distal end configured to engage within the shaft inner lumen and urge the at least two centering wires to extend into the at least two voids, wherein the centering wires contact a body channel when the wire centering sheath device is inserted into the body channel.

In another embodiment, a method of centering a wire centering sheath device within a body channel is disclosed, the method comprising: (a) preparing a body channel to receive a wire centering sheath device; (b) inserting a wire centering sheath device within a body channel, the device comprising a shaft, the shaft having a proximal end, a distal end, a sidewall, at least two slots forming at least two voids in the sidewall, and at least two centering wires connected to the shaft and disposed adjacent to the at least two slots, wherein the shaft includes a shaft inner lumen running from the proximal end to the distal end; and a hollow rod adapted for inserting into the proximal end of the shaft, the rod having a distal end configured to engage within the shaft inner lumen; (c) deploying the at least two centering wires by axially moving the rod within the shaft inner lumen so as to contact the at least two centering wires and urge the at least two centering wires to extend into the at least two voids and contact the body channel, wherein the wire centering sheath device is centered within the body channel.

In a further embodiment, a wire centering sheath system is disclosed, the system comprising: a shaft, the shaft having a proximal end, a distal end, a sidewall, an interior surface, at least three slots forming at least three voids in the sidewall, the at least three slots and at least three voids disposed at substantially equal radii of the longitudinal axis of the shaft, and at least three centering wires connected to the interior surface and disposed adjacent to the at least three slots, wherein the shaft includes an inner lumen running from the proximal end to the distal end; a hollow rod adapted for inserting into the proximal end of the shaft, the rod having a distal end configured to engage within the inner lumen and urge the at least three centering wires to extend into the at least three voids, wherein the rod further comprises a rod inner lumen configured to enable insertion of a medical instrument into the rod inner lumen; wherein the centering wires contact a body channel when the wire centering sheath device is inserted into the body channel.

The present disclosure can provide a number of advantages depending on the particular configuration. For example, the disclosed embodiments can reliably, accurately and effectively center a medical instrument or delivery device such as a catheter or wire.

These and other advantages will be apparent from the disclosure contained herein.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The terms "apparatus", "assembly", "device", "system", and variations thereof, as used herein, means a device used to center surgical devices, such as catheters.

The terms "determine", "calculate" and "compute," and variations thereof, as used herein, are used interchangeably and include any type of methodology, process, mathematical operation or technique.

The term "body channel" and "body cavity" and variations thereof, as used herein, means any of the spaces in a human or animal body to include veins and arteries.

The term "catheter" and variations thereof, as used herein, means a tubular instrument or device inserted into a body channel.

The term "catherization" and variations thereof, as used herein, means a process of inserting a tubular instrument or device into a body channel.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. The drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 1A is a partial cross-sectional side view of the wire centering sheath assembly with centering wires stowed according to a first embodiment;

FIG. 1B is a cross-sectional side view of the wire centering sheath assembly with centering wires stowed according to a first embodiment;

FIG. 1C is a cross-sectional end view of the wire centering sheath assembly with centering wires stowed at section A-A of FIG. 1B according to a first embodiment;

FIG. 1D is a cross-sectional end view of the wire centering sheath assembly with centering wires stowed at section B-B of FIG. 1B according to a first embodiment;

FIG. 2A is a partial cross-sectional side view of the wire centering sheath assembly with centering wires deployed according to a first embodiment;

FIG. 2B is a cross-sectional side view of the wire centering sheath assembly with centering wires deployed according to a first embodiment;

FIG. 2C is a cross-sectional end view of the wire centering sheath assembly with centering wires deployed at section A-A of FIG. 2B according to a first embodiment;

FIG. 2D is a cross-sectional end view of the wire centering sheath assembly with centering wires deployed at section B-B of FIG. 2B according to a first embodiment;

FIG. 3A is a partial cross-sectional side view of the wire centering sheath assembly with centering wires stowed according to a second embodiment;

FIG. 3B is a cross-sectional end view of the wire centering sheath assembly with centering wires stowed at section A-A of FIG. 3A according to a second embodiment;

FIG. 3C is a perspective view of the wire centering sheath assembly with centering wires stowed according to a second embodiment;

FIG. 3D is a perspective view of the wire centering sheath assembly with centering wires deployed according to a second embodiment;

FIG. 4A is a partial cross-sectional side view of the wire centering sheath assembly with centering wires stowed according to a third embodiment;

FIG. 4B is a cross-sectional end view of the wire centering sheath assembly with centering wires stowed at section A-A of FIG. 4A according to a third embodiment;

FIG. 4C is a perspective view of the wire centering sheath assembly with centering wires stowed according to a third embodiment;

FIG. 4D is a perspective view of the wire centering sheath assembly with centering wires deployed according to a third embodiment.

DETAILED DESCRIPTION

Figure 5:
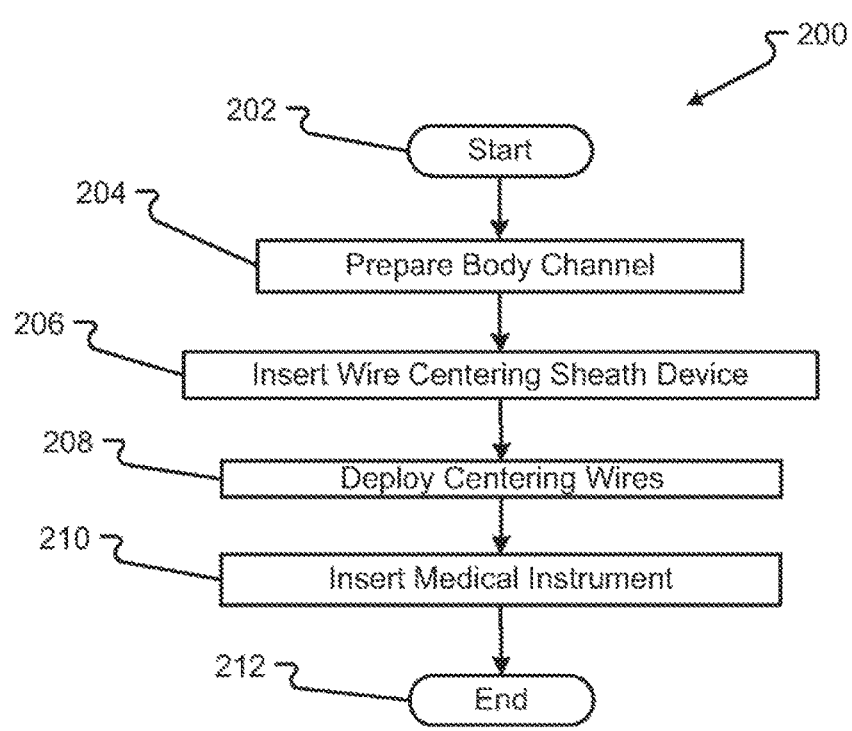
FIG. 5 is a flow diagram depicting a method of centering a medical instrument in accordance with embodiments of the disclosure.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising,"

or "having" and variations thereof herein is meant to encompass the items listed thereafter and equivalents thereof as well as additional items.

Embodiments of the present disclosure are directed to a wire centering sheath system in which wires extend radially from a sheath to brace against a body channel or body cavity. In some embodiments, the wire centering sheath system may be used to center surgical devices installed during vascular interventions. In some embodiments, the wires which outwardly extend from a sheath are generally disposed along a longitudinal axis of the device. In other embodiments, the wires which outwardly extend from a sheath are generally disposed in a spiral arrangement along a longitudinal axis of the device. In one embodiment, the method of use for centering a wire centering sheath system may include inserting a wire centering sheath device into a body channel and deploying centering wires by means of a rod inserted into an inner lumen of a shaft in which the centering wires are connected.

FIGS. 1A-D and 2A-D depict a wire centering sheath assembly or device 100 according to a first embodiment. Generally, FIGS. 1A-D depict the centering sheath assembly 100 with centering wires 170 stowed or not deployed (a first state of the device 100), and FIGS. 2A-D depict the centering sheath assembly 100 with centering wires 170 deployed or extended (a second state of the device 100). The wire centering sheath assembly 100 comprises a substantially cylindrical shaft 110 with shaft distal end 114, shall proximal end 118, shaft exterior surface 120, shaft interior surface 124 and shaft sidewall 126. The shaft 110 forms a shaft inner lumen 128 and includes a plurality of slots 130, each slot 130 forming a shaft sidewall void 127. The slots 130 are disposed substantially along a longitudinal axis of the shaft and disposed at substantially equal radii (i.e. 180 degree) of the longitudinal axis of the shaft. A plurality of centering wires 170 are disposed adjacent each slot 130 on the shaft 110 and secured to the shaft 110 by centering wire attachment pins 180. Each centering wire 170 comprises centering wire proximal end 174 and centering wire distal end 178. In one embodiment, each centering wire 170 is disposed adjacent each slot 130 on the shaft 110 and secured to the shaft 110 by centering wire attachment pins 180. Further, in one embodiment, each centering wire 170 is disposed adjacent each slot 130 on the shaft 110 and secured to the shaft interior surface 124 by centering wire attachment pins 180 at the centering wire distal end 178. In one embodiment, the centering wires 170 are of substantially circular cross-section.

The wire centering sheath assembly 100 further comprises a substantially cylindrical hollow rod 150 which is adapted for inserting into the inner lumen of the shaft 110. The rod 150 comprises a rod proximal end 154, rod distal end 158, rod distal end surface 159 and rod exterior surface 160. In one embodiment, the rod 150 comprises a rod end cap 155. In one embodiment, the rod 150 comprises a rod inner lumen 156, to allow, among other things, a surgical instrument such as a catheter to fit within the rod inner lumen 156. The rod exterior surface engages the shaft interior surface 124.

The wire centering sheath assembly 100 is configured to insert within a body cavity or channel 190 comprising a body channel interior surface 194.

Referring to FIG. 1A-D, the wire centering sheath assembly 100 is depicted with two centering wires 170 stowed, that is, in the first state of the device 100. In this state, the centering wires 170 are substantially in axial alignment with the shaft 100. In one embodiment, in such a first state of the device 100, the centering wires are in surface contact with the shaft interior surface 170 at one or both of the centering wire proximal end 174 and centering wire distal end 178, as depicted in FIG. 1C. Further, at least a portion of the centering wire 170, between the centering wire proximal end 174 and centering wire distal end 178, is disposed adjacent a slot 130 with associated shaft sidewall void 127, as depicted in FIG. 1D.

Referring to FIG. 2A-D, the wire centering sheath assembly 100 is depicted with two centering wires 170 deployed, that is, in the second state of the device 100. In this state, the centering wires 170 deform so as to penetrate the shaft sidewall void 127 as enabled by engagement with the rod distal end 158. In one embodiment, in such a second state of the device 100 the centering wires deform into a substantially arc-shaped profile so as to engage the body channel interior surface 194. More specifically, as depicted in FIG. 2B-D, the rod distal end surface 159 engages the centering wire proximal end 174 and urges a portion of the centering wire, between the centering wire proximal end 174 and centering wire distal end 178, into the slots 130 and associated shaft sidewall void 127, such that a portion of the centering wire engages the body channel interior surface 194.

Further, at least a portion of the centering wire 170, between the centering wire proximal end 174 and centering wire distal end 178, is disposed adjacent a slot 130 with associated shaft sidewall void 127, as depicted in FIG. 1D. In one embodiment, when the device 100 is in state two, the centering wires are under a compressive load.

In some embodiments, the rod 150 is any slide-based substantially cylindrical element with rod distal end surface 159 sufficient to engage the plurality of centering wires 170. In one embodiment, the rod 150 is any slide-based activation device as known to those skilled in the art. In another embodiment, the rod 150 is a screw-based activation device with rod distal end 158 sufficient to engage the plurality of centering wires 170. In one embodiment, the rod 150 is any screw-based or thumb wheel activation device as known to those skilled in the art.

In one embodiment, the deployment of the centering wires 170 is done by means other than a hollow rod 150. For example, the means may be by any mechanical, electrical, thermal or magnetic means known to those skilled in the art that urges the centering wires 170 to deploy. For example, the centering wires 170 may, in one embodiment, be temperature sensitive such that when heated, the wires deploy through the slots 130. In another embodiment, the centering wires 170 may have magnetic properties such that positioning of a magnetic input urges the centering wires 170 through the slots 130.

In one embodiment, one or more of the plurality of centering wires 170 are attached or connected to the shaft by a centering wire attachment 190 of substantially cylindrical cross-section. In other embodiments, the centering wire attachment 190 is by any means know to those skilled in the art, to include any bonding means such as glue and heat-adhesion, and interference fit slots or groove fits (to include, for example, tongue-and-groove fits) disposed on the shaft interior surface 124 such that the centering wire distal end 178 may be securely inserted.

In another embodiment, the one or more of the plurality of centering wires 170 and an associated identical number of are disposed substantially along a longitudinal axis of the shaft and disposed at substantially equal radii of the longitudinal axis of the shaft.

In another embodiment, the centering wires 170 and associated centering attachment pins 180 are reversed in that the centering attachment pins 180 are located at the centering wire proximal end 174, and the rod 150 is configured such that is passes over the centering wires 170, and after deployment of a widening collar or ring (not shown), is able to engage the centering wire distal end 178 and thereby deploy the centering wires as discussed above.

In one embodiment, the centering wires 170 are of substantially round cross-sectional shape. In one embodiment, the centering wires 170 are of substantially rectangular cross-sectional shape. In one embodiment, the centering wires 170 are of substantially triangular cross-sectional shape, either in which the apex of one side of the triangle is pointed up through the slot 130 or a base of the triangle is pointed up through the slot. In a one embodiment, the substantially triangular cross-sectional shaped centering wire 170 is an equilateral triangle. In one embodiment, the centering wire 170 is substantially flat. In one embodiment, the centering wire 170 has rounded edges.

In a preferred embodiment, the slots 130 are of rectangular shape of width preferably between about 100% and 120% of the width or diameter of the centering wire 170, more preferably between about 100% and 110% of the width or diameter of the centering wire 170, and most preferably between about 100% and 105% of the width or diameter of the centering wire 170.

In a preferred embodiment, the slots 130 are of rectangular shape of length preferably between about 90% and 20% of the total length of the stowed centering wire 170, more preferably between about 80% and 30% of the width or diameter of the centering wire 170, and most preferably between about 80% and 40% of the width or diameter of the centering wire 170.

In another embodiment, the slots 130 are of rectangular shape with circular ends. In another embodiment, the slots 130 are of an oval shape.

In one embodiment, the end of the centering wire 170 which engages with the rod distal end 158 is fitted with a stop means to prevent over-compression of the centering wire 170 so as to cause the centering wire 170 to deploy with a free end through the slot 130 and subsequently impact the body channel interior surface 194. Such a stop means could be any of those known to those skilled in the art to include a collar or ring fitted to the shaft interior surface 124 adjacent the slot 130 to prevent further travel of the rod 150.

In one embodiment, the centering wires 170, when deployed, do not significantly decrease in length, where significantly means a decrease of more than 10% of length. In one embodiment, the centering wires 170 are elastic, in that they return to their stowed state shape and size when returned from a deployed state. In embodiment, the centering wires 170 are sufficiently inelastic in that when deployed through urging of the rod 150, the centering wires 170 retain their deployed state shape and size.

FIG. 3A-D is a cross-sectional side view of the wire centering sheath assembly 100 in a second embodiment comprising three centering wires 170. FIG. 3A-C depict the device 100 with centering wires 170 in a first, or stowed, state. FIG. 3D depicts the device 100 with centering wires 170 is a second, or deployed, state. The three centering wires 170 are disposed at equal radial positions (i.e. at 120 degrees) within the shaft interior surface 124, as depicted in FIG. 3B. FIG. 3A-D depict wire centering sheath assembly 100 with shaft distal end 114, shaft proximal end 118, shaft inner lumen 128 and slots 130. Also depicted are rod 150, rod proximal end 154. FIG. 3D depicts the set of three centering wires 170 deployed to form a generally uniform arc-shape.

In other embodiments of the device 100 as depicted in FIG. 3A-D, the one or more plurality of centering wires 170, and the associated equal number of plurality of slots 130, are each more than (3) in number. That is, in one embodiment, there are four (4) centering wires 170 and four (4) slots 130. In another embodiment, there are five (5) centering wires 170 and five (5) slots 130. In another embodiment, there are six (6) centering wires 170 and six (6) slots 130. In another embodiment, there are at least six (6) centering wires 170 and at least six (6) slots 130.

FIG. 4A-D is a cross-sectional side view of the wire centering sheath assembly 100 in a third embodiment comprising three centering wires 170 and three spirally-disposed slots 130. That is, each of the three spirally-disposed slots 130 are disposed at an oblique angle (i.e. not zero degrees) from a longitudinal axis of the shaft 110 and disposed at substantially equal radii of the longitudinal axis of the shaft 100.

FIG. 4A-C depict the device 100 with centering wires 170 in a first, or stowed, state. FIG. 4D depicts the device 100 with centering wires 170 is a second, or deployed, state. The three centering wires 170 are disposed at equal radial positions (i.e. at 120 degrees) within the shaft interior surface 124, as depicted in FIG. 4B. FIG. 4A-D depict wire centering sheath assembly 100 with shaft distal end 114, shaft proximal end 118, shaft inner lumen 128 and slots 130. Also depicted are rod 150, rod proximal end 154. FIG. 4D depicts the set of three centering wires 170 deployed in a spiral configuration of an arc-shape. In a preferred embodiment, the three spirally-disposed slots 130 are oriented relative to the longitudinal axial dimension of the shaft 110 (where 0 degree is parallel alignment as depicted in FIGS. 1A, 2A and 3A and 90 degree is perpendicular to the longitudinal axial dimension of the shaft 110) at an oblique angle, that is other than zero (0) degrees.

In other embodiments of the device 100 as depicted in FIG. 4A-D, the one or more plurality of centering wires 170, and the associated equal number of plurality of spirally-disposed slots 130, are other than three (3) in number. That is, in one embodiment, there are two (2) centering wires 170 and two (2) spirally-disposed slots 130. In another embodiment, there are four (4) centering wires 170 and four (4) spirally-disposed slots 130. In another embodiment, there are five (5) centering wires 170 and five (5) spirally-disposed slots 130. In another embodiment, there are six (6) centering wires 170 and six (6) spirally-disposed slots 130. In another embodiment, there are at least six (6) centering wires 170 and at least six (6) spirally-disposed slots 130.

In one embodiment of the device 100 when configured with a plurality of spirally-disposed slots 130, the advancement of the rod 150 is configured such that engagement of the centering wires 170 so as to deploy the centering wires 170 through slots 130 and shaft sidewall voids 127 enables a corkscrewing effect. Stated another way, the edges of the centering wires 170 engage the body channel interior surface 194 such that the shaft distal end 114 advances distally (or forward or to the right in FIG. 4A or to the southeast in FIG. 4C-D) when the shaft 110 is rotated. In one embodiment, the rod 150 rotatably engages the shaft inner lumen 128 along a rod exterior surface and the shaft advances within the body chamber (and may further engage a lesion located on or within the body chamber) in a corkscrew manner.

FIG. 5 is a flow diagram depicting a method 200 of centering a medical instrument in accordance with embodiments of the disclosure. Generally, the method 200 starts at step 202 and ends at step 212.

At step 204, a body channel is prepared for surgical intervention. Depending on the location of the intervention area, an entry location is selected. For example, the jugular vein is a typical insertion point for medical interventions involving the treatment of venous disease, such as those developed in the inferior vena cava or the right femoral vein and left femoral vein. The method 200 then moves to step 206.

At step 206, the wire centering sheath device 100 is inserted into body channel 190. The exact location of the device 100 along a given body channel may be determined by any means known to those skilled in the art, to include radioactive marking techniques. The method then moves to step 208

At step 208, with the wire centering sheath device 100 positioned, the rod 150 engages the shaft inner lumen 128 so as to deploy the plurality of centering wires 170. The rod 150 may engage the shaft inner lumen 128 by any means know to those skilled in the art, to include as a slide-based activation means, a screw-based activation means and thumb wheel activation means. The rod 150 engages the shaft inner lumen 128 and subsequently engages or connects with the plurality of centering wires 170 so as to compress the centering wires 170 and urge there deployment through the slots 130 and associated shaft sidewall voids 127. The centering wires 170 continue to be compressed and urged outward from the shaft 110 until engaged with the body channel interior surface 194. In this deployed state, the wire centering sheath assembly 100 is centered within the body channel 190. The method 200 then enters step 210.

At step 210, with the wire centering sheath assembly 100 in a centering wire deployed state or mode, a medical instrument, such as a catheter, may be inserted through the center of the hollow rod 150 and out through the shaft distal end 114, and, for example, reliably, safely and effectively deliver its medical product from the center of the body channel 190. Alternatively, a medical intervention device could be inserted through the hollow rod 150 and out through the shaft distal end 114 so as to perform a medical intervention from the center of the body channel 190. The method 200 ends at step 212.

The materials of the device 100, such as the shaft 110 and rod 150, comprise materials that are biocompatible and biostable (e.g., non-dissolving in the body) and generally includes organic imperials such as polyurethane and polyimide. The centering wire 170 may comprise polymer materials and/or metallic materials to include stainless steel, titanium alloy, aluminum alloy, chromium alloy, and other metals or metal alloys, in a configuration and/or combination that is biocompatible and non-traumatic to the body chamber.

A number of variations and modifications of the disclosure can be used. It would be possible to provide for some features without providing others.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiment, includes providing devices and processes in the absence of items not depicted and/or described herein or in various embodiments hereof, including in the absence of such items as may have been used in previous devices or processes, e.g., for improving performance, achieving ease and or reducing cost of implementation.

The foregoing discussion has been presented for purposes of illustration and description. The foregoing is not intended to limit the disclosure to the form or forms disclosed herein. In the foregoing Detailed Description for example, various features are grouped together in one or more embodiments for the purpose of streamlining the disclosure. The features of the embodiments may be combined in alternate embodiments other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description has included description of one or more embodiments and certain variations and modifications, other variations, combinations, and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of centering a wire centering sheath device within a body channel comprising:
    (a) preparing a body channel to receive a wire centering sheath device;
    (b) inserting a wire centering sheath device within a body channel, the device comprising a shaft, the shaft having a proximal end, a distal end, a sidewall, at least two slots forming at least two voids in the sidewall, and at least two centering wires disposed adjacent to the at least two slots, wherein each of the at least two centering wires comprises a centering wire proximal end and a centering wire distal end, wherein one of the centering wire proximal end or the centering wire distal end is attached to the shaft, and the other one of the centering wire proximal end or the centering wire distal end is unattached to the shaft, wherein the shaft includes a shaft inner lumen running from the proximal end to the distal end; and a rod adapted for inserting into the proximal end of the shaft, the rod having a distal end configured to engage within the shaft inner lumen; and
    (c) deploying the at least two centering wires by axially moving the rod within the shaft inner lumen so the rod contacts the at least two centering wires and urges the at least two centering wires to extend into the at least two voids and contact the body channel, wherein the wire centering sheath device is centered within the body channel.

2. The method of claim 1, wherein the rod further comprises a rod inner lumen configured to enable insertion of a medical instrument into the rod inner lumen.

3. The method of claim 2, wherein the rod slideably engages the shaft inner lumen along a rod exterior surface.

4. The method of claim 1, wherein the at least two slots forming at least two voids in the sidewall are at least three slots forming at least three voids in the sidewall, and the at least two centering wires are at least three centering wires.

5. The method of claim 4, wherein the at least three slots are disposed substantially along a longitudinal axis of the shaft and disposed at substantially equal radii of the longitudinal axis of the shaft.

6. The method of claim 4, wherein the at least three slots are disposed at an oblique angle from a longitudinal axis of the shaft and disposed at substantially equal radii of the longitudinal axis of the shaft.

7. The method of claim 1, wherein the rod rotatably engages the shaft inner lumen along a rod exterior surface and the shaft advances within the body chamber in a corkscrew manner.

8. The method of claim 2, wherein the medical instrument is a catheter.

9. The method of claim 2, wherein the at least two centering wires atraumatically contact the body channel.

10. The method of claim 1, wherein the centering wire proximal end is attached to the shaft and the centering wire distal end is unattached to the shaft.

11. The method of claim 1, wherein the centering wire proximal end is unattached to the shaft and the centering wire distal end is attached to the shaft.

* * * * *